United States Patent [19]
Burruss

[11] Patent Number: 5,930,842
[45] Date of Patent: Aug. 3, 1999

[54] PROTECTIVE EAR COVERING

[76] Inventor: Nancy L. Burruss, 10511 Oakmoor La., Parker, Colo. 80134

[21] Appl. No.: 09/161,053

[22] Filed: Sep. 25, 1998

[51] Int. Cl.[6] .................................................. A61F 9/02
[52] U.S. Cl. ................... 2/452; 2/209; 2/909; 2/209.13; 2/DIG. 11
[58] Field of Search ................... 2/9, 19, 209, 439, 2/440, 452, 909, 209.13, 423, DIG. 11, 172

[56] References Cited

U.S. PATENT DOCUMENTS

| | | | |
|---|---|---|---|
| 869,741 | 10/1907 | Seitzman | 2/9 |
| 4,670,911 | 6/1987 | Dunford | 2/209 |
| 4,682,374 | 7/1987 | Geiser | 2/209 |
| 4,751,746 | 6/1988 | Rustin | 2/209 |

*Primary Examiner*—Diana L. Oleksa
*Assistant Examiner*—Katherine Moran
*Attorney, Agent, or Firm*—Lee G. Meyer; Patton Boggs, LLP

[57] ABSTRACT

An ear protection device made of an insulating fabric that adjustably and releasably fastens to the retaining strap of an eye goggles unit. The device utilizes elastic means to retain its lower edge proximate the head of the wearer under even severe conditions.

12 Claims, 2 Drawing Sheets

PROTECTIVE EAR COVERING

BACKGROUND OF THE INVENTION

1. Field of Invention

The present invention relates to a protective ear covering and more particularly to a protective ear covering device and assembly that is worn by attachment to a retaining strap on a pair of eye goggles.

2. Description of Related Art

Traditionally, a winter sports participant, such as a snowmobiler or skier, experiences rapid movement in a sub-zero environment requiring protection of both the eyes and the ears. A wide variety of eye protective wear and ear coverings are currently available for the winter sport enthusiast. Both devices have been technically improved to provide for example, protection from ultraviolet rays, sub-zero temperatures and the like. New materials provide resistance from breakage and greater thermal insulation, with less bulk and weight. However, despite such improvements, this market is still dominated by classical systems and styles of protection.

In choice of ear protection, the winter sports participant is limited to a hat, earmuffs or a headband. The traditional head band is a width of stretchable cloth, which encircles the head, sufficient to cover the ears of the wearer. It is separate from protective eye wear, such as ski goggles which have for example, a sealed lense element and an elastic retaining strap for attaching the end portions of the goggles and are adapted to fit around the wearer's head in order to retain the goggles in place. This arrangement of separate eye goggles/head gear present a myriad of problems. First, each device of the separate head band/eye apparel arrangement competes for position on the head of the wearer. Thus, adjusting the goggles displaces the head band and vice versa. Second, the ear protector is essentially of constant width around the head, interfering with the coiffe or hairdo of the wearer yielding "ski hair", "hat head" or "head band hair." The alternative to the head band is a hat, ear muffs or simply having cold ears.

By combining the retention strap of the goggles and the ear covering, some of the inherent problems discussed above have been eliminated, however, none to date have been totally satisfactory. Specifically, though several inventions have tried to overcome these limitations, they maintain some of the basic limitations which have prevented more effective means of providing warmth, comfort and convenience to the wearer.

U.S. Pat. No. 5,421,037 to Schulze discloses a combined goggles and headband assembly comprising a goggles unit having a retaining strap for encircling the head of a wearer, and a cover for the ears of the wearer formed from a single piece of cloth of a length and width to encircle the retaining strap from opposed end edges of the goggles. A blank piece of cloth sized to completely encircle the retaining strap from opposed side edges of the goggles, and to cover the wearer's ears at the same time, employs cooperative releasable fastening means secured to both the longitudinal dimension of strips as well as the latitudinal dimensions of the cloth to provide for releasable securement of the cloth to the retaining strap.

This device suffers from a myriad of draw backs. First the ear piece is not retained around the ears of the wearer. Thus, as the skier or snowmobiler gains speed the wind picks up the material proximate the ears and blows it outward giving a "Snoopy" effect and exposing the ears of the wearer. Further, the means for attaching the cloth to the retaining strap allows no adjustment for cinching the cloth to the strap. The ear covering is able to twist with respect to the strap becoming uncomfortable to the wearer and again exposing the wearer's ears.

U.S. Pat. No. 5,617,589 to Lacore et al. describes a pair of sporting goggles with a headband which also serves as a type of "earmuff"g. This device incorporates the covering of the ears into the band itself, not allowing for the removal of such covering without removing the entire goggles assemblage.

U.S. Pat. No. 5,625,903 to Schultz et al. discloses a headband with adjustable speakers. This invention provides the means to listen to a remote transmission while permitting the adjustment of the speakers by means of the headband. However, this device is not intended to simply provide coverage for the ears, but rather it provides the means to satisfactorily place the speakers adjacent to the wearer's ears. This device is costly due to the speakers, and fails to address the need for simple, suitable covering for the ears.

U.S. Pat. No. 5,713, 078 to De Angelis describes a headband and goggles device that is intended to protect the ears of the wearer from the entry of water during participation in various water sports and activities. This device, however, is made of a waterproof material and must be water tight on the head, restricting hearing and ventilation. The design of this invention is specific to the need of those with an aversion to water entering the ear canal, and does not provide insulation from the cold or other similar elements.

Thus, it would be advantageous to have a device or appliance that covers and protects the ears, even under extreme conditions of advanced down hill skiing or snowmobiling, is able to be removed during weather not requiring ear protection or reasons of fashion, for example, a change of color of skiing apparel and can be effectively attached to any width of a goggle retaining strap.

SUMMARY OF THE INVENTION

The present invention contemplates an ear protection device having an ear protecting element attached to a retaining strap securing element which is releasably fastened to the retaining strap of an eye goggles unit. The device is adapted to attach to an eye goggles unit having, for example, an integral, unitary lens portion for covering a wearer's eyes and an adjustable elastic retaining strap for encircling a wearer's head.

In the broad aspect the ear protection device of the instant invention comprises a retaining strap attaching or securing element and an ear protecting or covering element wherein the retaining strap securing element is adapted for cinching engagement of the goggles retaining strap in a manner such that the ear protecting element, which contains an elastic means along the periphery thereof, is maintained proximate the ears of the wearer.

The retaining strap securing element comprises a piece of flexible material sized to completely encircle the goggle retaining strap, preferably engaging the strap from the opposed side edges of the goggles, having cooperative releasable fastening strips which are secured to appropriate portions of the flexible material to provide for adjustable or cinching, releasable securement to the goggles retaining strap.

The ear protecting element is supported and maintained in place by being attached to the retaining strap securing element along the longitudinal base thereof such that the ear protecting element is secured proximate to and covering the wearer's ears. Elastic means encircle the lower longitudinal edge of the ear protecting element to retain the lower edge of the ear covering portion of the element in encasing engagement with the wearer's ears and proximate the head of the wearer. The ear covering portions of the ear covering element are elongated to provide covering of the wearer's ears while the portion encircling the head of the wearer is truncated to provide the least interference with the wearer's hair. In a preferred embodiment the ear protecting element contains an elongated cloth portion proximate the ears of the wearer to fully cover the ears while reducing the width of the retaining strap securing element around the rear of the wearer's head.

In one embodiment, the flexible material of the retaining strap securing element is of a shape with cooperative, releasable fasteners being secured on one face thereof, such that upon a doubling over of the cloth, the edges are connected to each other, forming and leaving a longitudinal passage interior therein to receive and embrace the retaining strap. The releasable fasteners are adapted to adjustably cinch the strap. In a preferred embodiment the releasable fasteners are hook and fiber type fasteners.

Other aspects and features of the present invention will become apparent from a reading of the following detailed description of a preferred embodiment, the following claims and inspection of the various figures of the drawing, all of which are a part of the present disclosure.

BRIEF DESCRIPTION OF THE DRAWINGS

Other advantages of this invention will be apparent from the following specification, claims, and drawings, in which:

DETAILED DESCRIPTION OF THE INVENTION

Figure 1:
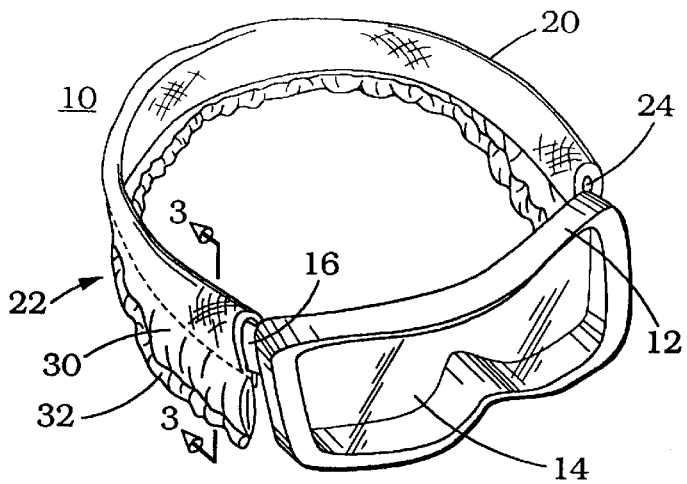
FIG. 1 is an elevated perspective view of one embodiment of the ear protection device positioned on the retaining strap of a goggles unit.

Referring now, particularly to FIGS. 1–4, wherein like parts are referred to with like reference numerals, there is shown a preferred embodiment of the instant invention.

Figure 2:
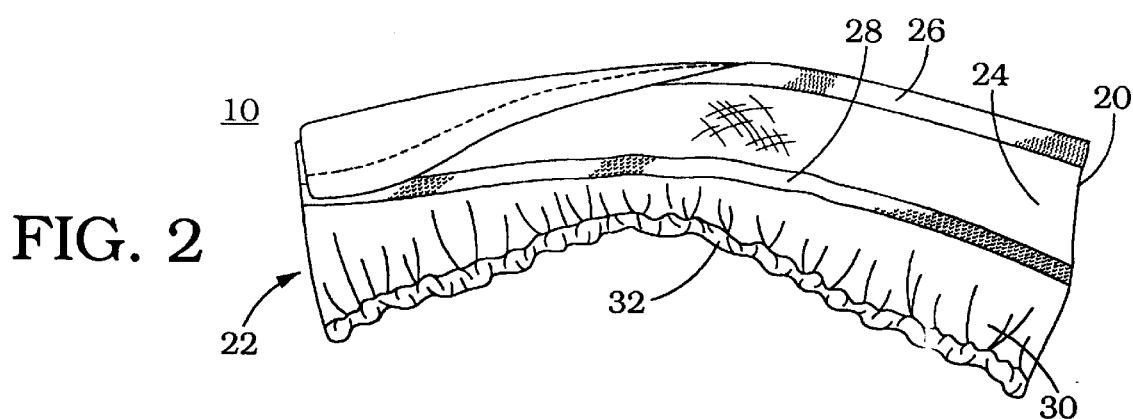
FIG. 2 is a perspective view of the embodiment of FIG. 1 showing the cooperative releasable fastening arrangement of the head band attaching element in a partially open position.

Turning to FIG. 2, there is shown the ear protection device 10 in accordance with the instant invention. The ear protection device 10 is adapted for releasable, cinching attachment as shown in FIG. 1 to a goggles unit 12. The goggles unit 12 comprises an integral, unitary eyepiece or lens element 14 for covering a wearer's eyes with suitable indentation for the wearer's nose, and an adjustable elastic retaining strap 16 having two ends, one attached to either side of the unitary eyepiece or lense element 14, for encircling a wearer's head, so as to hold the goggles unit 12 securely over the wearer's eyes.

The ear protection device 10 is adapted for releasable, cinching securement to the elastic retaining strap 16 while covering the ears of the wearer and comprises a retaining strap securing element 20 attached to an ear protecting element 22. The ear protection device 10 is preferably fabricated of a relatively warm fabric such as 100% knitted acrylic fabric. The fabric may be wool, cotton or blends thereof, including acrylic in the blends.

Figure 3:
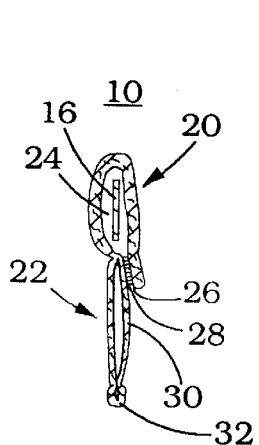
FIG. 3 is a cross-sectional view of the ear protection device shown along the line 3—3 of FIG. 1.

As seen in FIG. 3, the ear protection device 10 comprising a retaining strap securing element 20 is attached to the ear protecting element 22 along the lower longitudinal edge of the retaining strap securing element 20 and the upper longitudinal edge of the ear protecting element 22. Thus, the attachment means as further described below, is not an integral part of the ear protecting element 22 allowing adjustment of the retaining strap securing element 20 about elastic retaining strap 16 without effecting the functionality of ear protecting element 22.

As better seen in FIG. 2, the retaining strap securing element 20 is of a flexible material adapted to form a longitudinal adjustable channel 24 for receiving the elastic retaining strap 16. The longitudinal, adjustable channel 24 has a width represented by the distance between its first and second side edges 26 and 28. The width of the longitudinal channel 24 is such that the first side edge 26 may be folded along the entire width of the elastic retaining strap 16 to engage the second side edge 28 to form an elongated, adjustable retaining passage therein so as to completely encircle the elastic retaining strap 16 along its entire length. The longitudinal, channel 24 is adjustable to cinch the retaining strap 16 along its entire length. The length of the retaining strap securing element 20 between the end edges proximate the unitary eyepiece or lens element 14 is sized to be substantially the same length as that of the elastic retaining strap 16. The width of the retaining strap securing element 20 between its first and second side edges 26 and 28 is sufficient such that, upon the retaining strap securing element 20 being folded upon itself along its longitudinal axis, the resulting width, allows the longitudinal channel 24 to be formed circumferentially about the elastic retaining strap 16. To ensure securement of the retaining strap securing element 20 in its engaging condition about the elastic retaining strap 16, cooperating, releasable fasteners, such as hook and fiber fasteners (e.g. Velcro), are placed on opposing surfaces of first side edge 26 and second side edge 28. One or both of such fasteners are of sufficient area to allow adjustment of the retaining strap securing element 20 about elastic retaining strap 16 by widening or narrowing formed longitudinal channel 24. Thus, as shown in FIG. 2, upon the retaining strap securing element 20 being folded, over the elastic retaining strap 16, the first and second side edge strips 26 and 28 cooperatively engage each other substantially the entire length of the elastic retaining strap 16, so as to secure the retaining strap securing element 20 about the elastic retaining strap 16 by means of the cinching effect of longitudinal channel 24.

Thus, when folded over the elastic retaining strap 16, as described above, the first and second side edges 26 and 28 provide for adjustable and releasable cinching securement of said ear protecting element 22, which is attached to the elastic retaining strap 16 by means of retaining strap securing element 20. The ear protecting element 22, which continues from said retaining strap securing element 20 along the lower longitudinal edge of said retaining strap securing element 20, covers the wearer's ears. The ear protecting element 22 comprises an ear protecting region 30 and an elastic means 32 which encircles a lower longitudinal edge of said ear protecting element 22 to retain said lower edge of said ear protecting element 22, and particularly the lower portion of the ear protecting region 30, proximate the head of the wearer 18.

Figure 4:
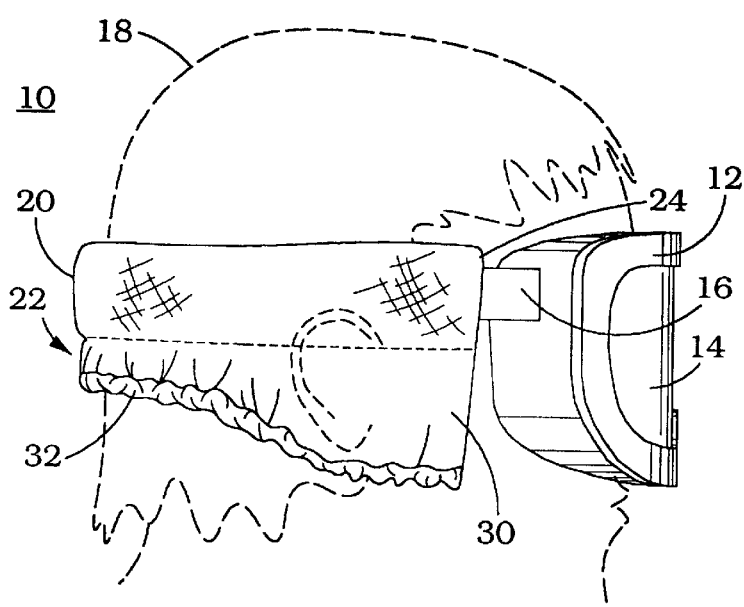
FIG. 4 is a side view of the ear protection device of FIG. 1 as worn by a wearer.

As better seen in FIG. 4, the ear protecting element 22 is formed in a configuration to provide protection for wearer's ears, but is of reduced width at the back of the head of wearer 18. This provides a snug fit by effecting an elastic tensioning about the back of the head of wearer 18 proximate the elastic retaining strap 16. In this manner the ear protecting region 30 is retained against the wearer's ears even when the wearer is subjected to wind force from for example, movement as in skiing or snowmobiling. The ear protecting region 30 is generally U-shaped in configuration, and with the elongated ear covering portions is preferably constructed out of a soft flexible insulating material to prevent chafing of the wearer's ears. Suitable materials are acrylic, cotton, synthetics, or blends thereof.

Referring to FIGS. 5–8, wherein like parts are referred to with like reference numerals there is shown another embodiment of the invention demonstrating extended and elongated ear covering regions.

Figure 5:
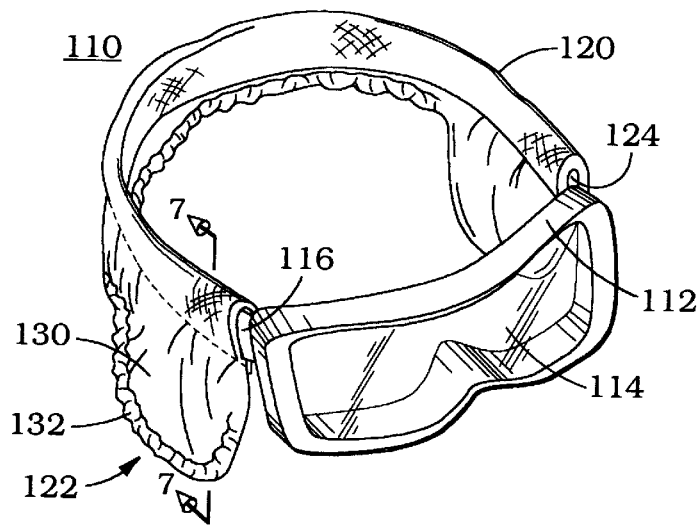
FIG. 5 is an elevated perspective view of another embodiment of the ear protection device positioned on the retaining strap of a goggles unit.
Figure 6:
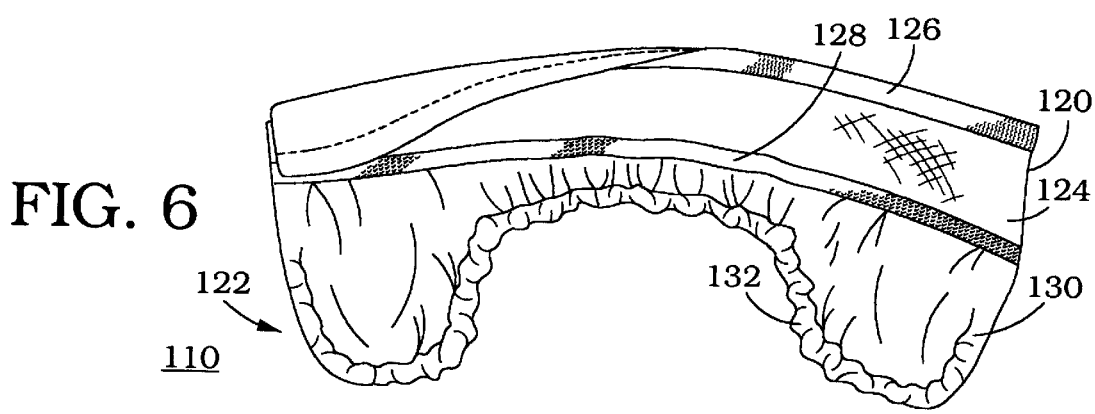
FIG. 6 is a perspective view of the embodiment of FIG. 5 showing the cooperative releasable fastening arrangement of the head band attaching element in a partially open position.

Turning to FIG. 5, there is shown the ear protection device 110 in accordance with the instant invention. The ear protection device 110 is adapted for releasable, cinching attachment as shown in FIG. 5 to a goggles unit 112. The goggles unit 112 comprises an integral, unitary eyepiece or lens element 114 for covering a wearer's eyes and an adjustable elastic retaining strap 116 having two ends, one attached to either side of the unitary eyepiece or lense element 114, for encircling a wearer's head. The ear protection device 110 is releasably and adjustably fastened to the elastic retaining strap 116 of the goggles unit 112 and is preferably constructed of a soft, flexible insulating material to prevent chafing of the wearer's ears. Suitable materials are acrylic, cotton, synthetics, or blends thereof.

Figure 7:
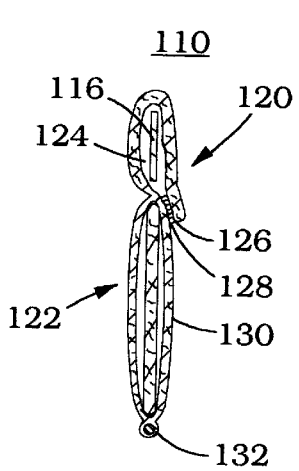
FIG. 7 is a cross-sectional view of the ear protection device along the line 7—7 of FIG. 5; and, FIG. 8 is a side view of the ear protection device of FIG. 5 as worn by a wearer.
Figure 8:
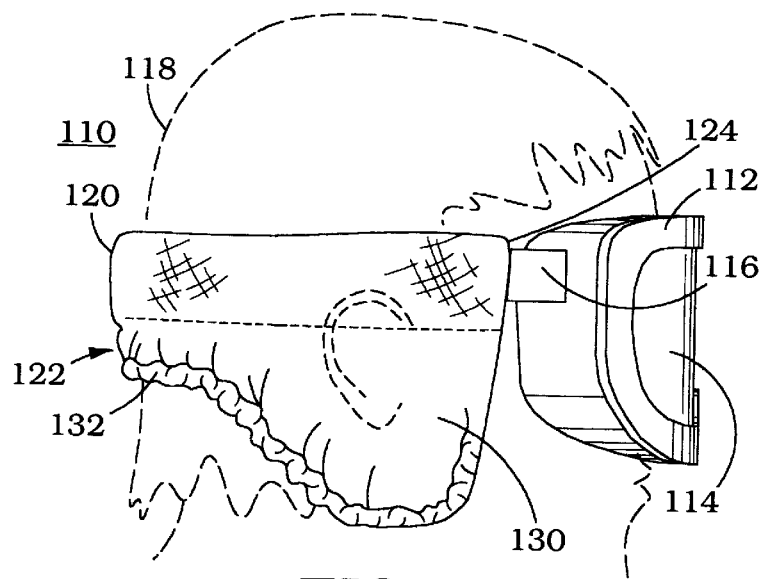

As better seen in FIG. 7, the ear protection device 110 comprises a retaining strap securing element 120 attached to an ear protecting element 122. The retaining strap securing element 120 is of a flexible material adapted to form a longitudinal channel 124 for receiving the elastic retaining strap 116 as previously described in FIG. 2. The longitudinal channel 124 has a width represented by the distance between its first and second side edges 126 and 128. The width of the longitudinal channel 124 is such that the first side edge 126 may be folded along the entire width of the elastic retaining strap 116 to engage the second side edge 128 to form an elongated retaining passage therein so as to completely encircle the elastic retaining strap 116 along the entire length of the elastic retaining strap 116.

When folded over the elastic retaining strap 116, as described above, the first and second side edges 126 and 128 provide for adjustable and releasable securement of said ear protection unit 110 to said elastic retaining strap 116 an ear protecting region 132 which continues from said retaining strap securing element 120 along a lower longitudinal base of said retaining strap securing element 120, to cover the wearer's ears; and, an elastic means encircling a lower longitudinal edge of said ear protecting region 130 to retain said lower edge of said ear protecting region 130 proximate the head of the wearer 118.

What is claimed is:

1. An ear protective device in combination with a goggles unit which includes a lens portion having opposed end edges for placement over a wearer's eyes and a goggles retaining strap having opposed ends connected to said opposed edges, respectively and encircling a wearer's head to retain the lens portion over the wearer's eyes comprising:

a) an ear protecting element, having an elastic means along the periphery thereof; and, b) a retaining strap securing element adapted for releasable cinching attachment to said goggles retaining strap and attachment to said ear protecting element such that said ear protecting element is maintained proximate the ears of the wearer.

2. The ear protective device of claim 1 wherein said retaining strap securing element comprises a piece of flexible material sized to completely encircle the goggle retaining strap to engage the retaining strap from the opposed side edges of the goggles, having cooperative releasable fastening strips which are secured to appropriate portions of said flexible material to provide for adjustable, cinching, releasable securement to the goggles retaining strap.

3. The ear protective device of claim 2 wherein the releasable fastening strips are hook and fiber type fasteners.

4. The ear protective device of claim 1 wherein said ear covering element has ear covering portions which are elongated to provide covering of the wearer's ears and a head encircling portion for encircling the head of the wearer which is truncated.

5. An ear protection device having an ear protecting element, having an elastic means along the periphery thereof, attached to a retaining strap securing element for releasably fastening said ear protective device to the retaining strap of an eye goggles unit.

6. The ear protective device of claim 5 wherein said retaining strap securing element comprises a piece of flexible material sized to completely encircle the goggle retaining strap to engage the retaining strap from the opposed side edges of the goggles, having cooperative releasable fastening strips which are secured to appropriate portions of said flexible material to provide for adjustable, cinching, releasable securement to the goggles retaining strap.

7. The ear protective device of claim 6 wherein the releasable fastening strips are hook and fiber type fasteners.

8. The ear protective device of claim 5 wherein said ear protecting element has ear covering portions which are elongated to provide covering of a wearer's ears and a head encircling portion for encircling the head of the wearer which is truncated.

9. An ear protection device comprising a retaining strap attaching element and an ear covering element, having an elastic means along the periphery thereof, wherein the retaining strap securing element is adapted for cinching engagement to the elastic retaining strap of a pair of eye goggles in a manner such that the ear protecting element is maintained proximate the ears of a wearer.

10. The ear protective device of claim 9 wherein said retaining strap attaching element comprises a piece of flexible material sized to completely encircle the goggle retaining strap to engage the retaining strap from the opposed side edges of the goggles, having cooperative releasable fastening strips which are secured to appropriate portions of said flexible material to provide for adjustable, cinching, releasable securement to the goggles retaining strap.

11. The ear protective device of claim 10 wherein the releasable fastening strips are hook and fiber type fasteners.

12. The ear protective device of claim 9 wherein said ear covering element has ear covering portions which are elongated to provide covering of the wearer's ears and a head encircling portion for encircling the head of the wearer which is truncated.

* * * * *